United States Patent
Fuhr et al.

(10) Patent No.: US 10,987,673 B2
(45) Date of Patent: Apr. 27, 2021

(54) TEMPERATURE-CONTROL ELEMENT FOR A MULTIWELL PLATE AND METHOD AND DEVICE FOR FREEZING AND/OR THAWING BIOLOGICAL SAMPLES

(71) Applicant: Fraunhofer-Gesellschaft zur Foerderung der angewandten Forschung e. V., Munich (DE)

(72) Inventors: Guenter R. Fuhr, Berlin (DE); Heiko Zimmermann, Waldbrunn (DE)

(73) Assignee: Fraunhofer-Gesellschaft zur Foerderung der angewandten Forschung e. V., Munich (DE)

( * ) Notice: Subject to any disclaimer, the term of this patent is extended or adjusted under 35 U.S.C. 154(b) by 531 days.

(21) Appl. No.: 15/532,995

(22) PCT Filed: Nov. 6, 2015

(86) PCT No.: PCT/EP2015/002232
§ 371 (c)(1),
(2) Date: Jun. 2, 2017

(87) PCT Pub. No.: WO2016/091344
PCT Pub. Date: Jun. 16, 2016

(65) Prior Publication Data
US 2017/0333905 A1 Nov. 23, 2017

(30) Foreign Application Priority Data
Dec. 10, 2014 (DE) .................... 102014018308.4

(51) Int. Cl.
*B01L 7/00* (2006.01)
*A01N 1/02* (2006.01)
(Continued)

(52) U.S. Cl.
CPC .............. *B01L 7/50* (2013.01); *A01N 1/0252* (2013.01); *A01N 1/0284* (2013.01);
(Continued)

(58) Field of Classification Search
CPC .......... B01L 7/50; B01L 7/54; B01L 3/50851; B01L 9/523; B01L 2200/025;
(Continued)

(56) References Cited

U.S. PATENT DOCUMENTS

| 6,376,233 B1 | 4/2002 | Wolf et al. |
| 8,945,881 B2 | 2/2015 | Arciniegas et al. |

(Continued)

FOREIGN PATENT DOCUMENTS

| DE | 10203940 B4 | 6/2006 |
| EP | 0612621 A1 | 12/1997 |

(Continued)

OTHER PUBLICATIONS

English language abstract for EP 2492663 A2 (2012).
(Continued)

*Primary Examiner* — Benjamin R Whatley
(74) *Attorney, Agent, or Firm* — Caesar Rivise, PC

(57) ABSTRACT

The invention relates to a temperature-control element (4) for a multiwell plate (1), which comprises a plurality of cavities (2) arranged in rows and columns for freezing and/or thawing biological samples. The temperature-control element (4) comprises a base body (6) which is made of a thermally conductive material and is flown through by a temperature-control fluid; and a plurality of protruding temperature-control fingers (5) arranged in rows and columns on an upper side of the base body (6), which are connected in a thermally conductive manner to the base body (6), wherein a grid spacing of the temperature control fingers (5) corresponds to a grid spacing of the cavities (2) of the multiwell (Continued)

plate (1). The invention further relates to a device and method for freezing biological samples, in particular for cryopreservation, and/or thawing biological samples, in particular a cryopreserved sample.

24 Claims, 8 Drawing Sheets

(51) Int. Cl.
 *B01L 3/00* (2006.01)
 *B01L 9/00* (2006.01)
 *C12M 1/00* (2006.01)
 *G01N 1/44* (2006.01)
 *G01N 35/00* (2006.01)

(52) U.S. Cl.
 CPC ............. *B01L 3/50851* (2013.01); *B01L 7/54* (2013.01); *B01L 9/523* (2013.01); *C12M 45/22* (2013.01); *G01N 1/44* (2013.01); *B01L 2200/025* (2013.01); *B01L 2200/0673* (2013.01); *B01L 2200/16* (2013.01); *B01L 2300/0829* (2013.01); *B01L 2300/185* (2013.01); *B01L 2300/1822* (2013.01); *B01L 2300/1827* (2013.01); *B01L 2300/1838* (2013.01); *B01L 2300/1894* (2013.01); *B01L 2400/0677* (2013.01); *G01N 2035/00445* (2013.01)

(58) Field of Classification Search
 CPC ......... B01L 2200/0673; B01L 2200/16; B01L 2300/0829; B01L 2300/1822; B01L 2300/1827; B01L 2300/1838; B01L 2300/185; B01L 2300/1894; B01L 2400/0677; A01N 1/0252; A01N 1/0284; C12M 45/22; G01N 1/44; G01N 2035/00445
 See application file for complete search history.

(56) References Cited

U.S. PATENT DOCUMENTS

| | | | |
|---|---|---|---|
| 9,180,597 B1 * | 11/2015 | Henry | ........................ B01L 1/04 |
| 2001/0034064 A1 | 10/2001 | Turner et al. | |
| 2004/0191896 A1 | 9/2004 | Miao et al. | |
| 2005/0009070 A1 | 1/2005 | Arciniegas et al. | |
| 2006/0063122 A1 | 3/2006 | Heeg et al. | |
| 2006/0228268 A1 | 10/2006 | Heimberg et al. | |
| 2007/0172396 A1 | 7/2007 | Neeper et al. | |
| 2010/0203595 A1 | 8/2010 | Ward et al. | |
| 2010/0311616 A1 | 12/2010 | Ozawa et al. | |
| 2012/0264206 A1 | 10/2012 | Heimberg et al. | |

FOREIGN PATENT DOCUMENTS

| | | | |
|---|---|---|---|
| EP | 1202805 | A1 | 5/2002 |
| EP | 1274301 | B1 | 11/2004 |
| EP | 2127751 | A1 | 12/2009 |
| EP | 2492663 | A2 | 8/2012 |
| EP | 2520369 | A1 | 11/2012 |
| JP | 53037480 | A | 4/1978 |
| JP | 2007040986 | A | 2/2007 |
| WO | 9820974 | A1 | 5/1998 |
| WO | 0009255 | A2 | 2/2000 |
| WO | 0045953 | A1 | 8/2000 |
| WO | 0108800 | A1 | 2/2001 |
| WO | 2004045772 | A2 | 6/2004 |

OTHER PUBLICATIONS

English language abstract for DE 10203940 A1 (2003).
International Search Report from corresponding PCT/EP2015/002232 dated May 30, 2016.
Partial Translation for JP 53037480 A (1978).
Machine Translation for JP 2007040986 A (2007).
Japanese Office Action dated Mar. 5, 2019 with Translation.

* cited by examiner

TEMPERATURE-CONTROL ELEMENT FOR A MULTIWELL PLATE AND METHOD AND DEVICE FOR FREEZING AND/OR THAWING BIOLOGICAL SAMPLES

CROSS-REFERENCE TO RELATED APPLICATIONS

This application is a U.S. National Phase Application of PCT/EP2015/002232, filed Nov. 6, 2015, which claims priority from DE 10 2014 018 308.4, filed Dec. 10, 2014, the contents of which applications are incorporated herein by reference in their entireties for all purposes.

BACKGROUND OF THE INVENTION

The invention relates to a temperature-control body for a multiwell plate. Furthermore, the invention relates to an apparatus and a method for freezing of biological samples, in particular for cryopreservation, and/or for thawing of biological samples, in particular a cryopreserved sample.

The increasing spread of institutional and commercial cryobanks, in particular for the storage of living cell material with sample numbers ranging from a few tens of thousands to several million requires automation of the process sequences. On the one hand this is necessary in order to achieve cost-effective storage conditions and on the other hand for the systematic implementation of SOP conditions (SOP: Standard Operation Procedure), for seamless documentation and for excluding subjective influences through laboratory personnel, as currently increasingly required in the field of biomedicine.

In the pharmaceutical sector, in medicine and in large parts of biotechnology automated sample receiving standards have become established which mainly came about during the developments of high-throughput screening (so-called SBS standard). Here, used in laboratory practice are multiwell substrates of very small, round comb structures forming reaction spaces, also known as wells, cavities or cups, being arranged in rows and columns, into which smallest portions of a sample, e.g. cell material, a blood sample etc. are introduced. These are flat plastic multiwell substrates with 6, 8, 16, 24 to 96 and more individual wells. These formats have in the meantime been globally standardized and are used in pipetting machines, cell culture machines and also in the device platform in analysis technology as well as diagnostics.

Such multiwell substrates are also known as multiwell plates or micro-titer plates. In accordance with the ANSI standard as recommended by the Society for Biomolecular Screening (SBS), the precise dimensions (length×width×height) are 127.76 mm×85.48 mm×14.35 mm. On the recommendation of the Society for Biomolecular Screening (SBS), ANSI published standards for micro-titer plates which, in particular, relate to the dimensions and positions of the recesses in micro-titer plates with 96, 384 and 1536 recesses. These are the standards ANSI/SBS 1 to 4—2004 and the standard SBS-6—2009.

Increasingly forming part of the chain of processing, characterizing and handling samples in medicine, pharmaceuticals development and biotechnology are cryo-biobanks in which samples, in particular living cells and stem cells from animals and humans are stored, and, if required, utilized again. This generally takes place by means of cryopreservation, defined freezing and thawing protocols as well as a storage temperature below −140° C., though in individual tubes, straws, individual plastic containers etc. so that the suspensions located in the well substrates have to be removed and transferred.

As numerous experiments have shown, the quality of a biological sample decreases with every transfer, especially if cells grow adhering to surfaces, as these have to be released through enzyme treatment or mechanical treatment and are thereby subject to not inconsiderable stress. It is also important that all the samples of a well plate, e.g. with 96 wells, are treated in the same or pre-definable way and can thus also be frozen, stored and thawed out.

From practice both controlled cooling and also heating systems are known, such as the "Gyro Freezers" by the company Planar Plc with programmable temperature programs or simple cryoboxes such as the "Mr. Frosty" cryobox by the company ThermoFischer Scientific Inc. Particularly in the case of important medical cell types such as immune cells, stem cells, especially IPS cells (Induced Pluripotent Stem Cells) controlled freezing and thawing protocols have recently proven to be of extreme importance for the quality of the sample and its vitality. Here, very good results have been achieved with very rapid cooling and heating. All this and in particular cooling and heating below 1°/sec are so far not available for multiwell substrates, for which reason the biological samples have to be transferred to other containers. But in the conventional plastic tubes, due to the thickness of the plastic wall and arrangement of the volumes, such exact, but above all rapid temperature courses cannot be achieved either.

It is therefore the objective of the invention to provide an improved apparatus for freezing of biological samples, in particular for cryopreservation, and/or for thawing of biological samples, in particular a cryopreserved sample with which the drawbacks of conventional techniques are avoided and which makes cryopreservation with rapid cooling and/or heating as well an increased vitality rate possible. A further objective is to provide such an apparatus which can be integrated in a process-efficient manner into automated high-throughput processes, e.g. high-throughput screening processes. It is also an objective of the invention to provide an improved method of freezing biological samples, in particular for cryopreservation and/or thawing biological samples, in particular cryopreserved samples with which vitality-influencing drawbacks of conventional techniques are overcome and which, in particular, makes simple post-processing of the thawed biological samples possible.

These objectives are achieved by the apparatuses and methods of the invention and will be described in more detail in the following description with partial reference to the figures.

SUMMARY OF THE INVENTION

In accordance with a first aspect of the invention a temperature-control body for a multiwell plate is provided for freezing and/or thawing samples, in particular biological samples located in the cavities of the multiwell plate. As known as such, the multiwell plate has a plurality of cavities arranged in rows and columns.

The temperature-control body according to the invention comprises a base body, through which a temperature-control fluid can flow, which is preferably made of a thermally conductive material, preferably with a high thermal capacity, and a plurality of protruding temperature-control fingers arranged in rows and columns on an upper side of the base body wherein a grid spacing of the temperature-control fingers corresponds to a grid spacing of the cavities of the multiwell plate. The spacing between adjacent temperature-control fingers thus corresponds with the spacing between adjacent cavities.

The invention therefore comprises the general technical teaching of providing a temperature-control body which is adapted to the matrix-like regular arrangement of the cavities of the multiwell plate and for this comprises a corresponding matrix-like arrangement of temperature-control fingers in the grid dimension of the arrangement of the cavities. Here, the face ends of the cooling fingers can be brought into connection with the base plates of the cavities, wherein preferably one temperature-control finger can be assigned to one cavity. The temperature-control fingers be rod or stud-shaped and the face ends of the temperature-control fingers are designed so that they form flat supports for the bases of the cavities of the multiwell plate.

A particular advantage of the invention is thus the fact that for freezing and thawing samples no longer have to be transferred into individual tubes, straws or special plastic containers etc. but by means of the temperature-control body according to the invention can be frozen and then thawed out again directly in and with the multiwell plate. Through this the vitality rate in the cryopreservation of biological samples can be increased. A further advantage is that temperature-control bodies designed in this way allow rapid freezing and/or thawing as the temperature-control fingers can be positioned very close to the sample and high cooling and heating rates can be generated directly in the biological sample via the base wall of the cavities.

The time-consuming transferring into separate freezing containers is also omitted and, instead, in one process chain commercially available multiwell plates can be used throughout so that the processing speed and efficiency, particularly for high-throughput methods, can be increased.

The term "sample" denotes any object which undergoes cryopreservation in the cavity. The sample material typically includes biological material such as cells, tissue, cell components or biological macromolecules as well as, if applicable, a nutrient solution, reagents, cryoprotection agents or other substances.

According to a variant of the invention, an electrically controllable heating and/or cooling element can be integrated into at least some of the temperature-control fingers, preferably into all. Examples of such heating elements can also be microwave or high-frequency elements which when controlled appropriately can bring about a defined introduction of heat against the fluid cooling of the base body. This variant provides the advantage that individual temperature-control fingers or partial groups of temperature-control fingers, for example, individual rows and/or columns, can be differently temperature-controlled. Through this the heat or cold input can be specifically varied via the arrangement of the cavities and adapted to the samples stored in the individual cavities.

According to a further variant, for monitoring the heat or cold input into the cavities there is the possibility of a temperature sensor, such as a thermoelectric sensor, being integrated into the end face of at least one of the temperature-control fingers. For example the temperature sensor can be designed as a flat version of a platinum resistance temperature sensor, such as a PT 100 or PT 1000 sensor.

In order to achieve as rapid freezing and thawing of the samples as possible it is advantageous if the end faces of the temperature-control fingers are highly polished, preferably with a roughness of under 20 µm and/or have a coating with a high thermal conductivity, preferably with a thermal conductivity comparable to that of copper or silver, preferably a coating of graphite or diamond.

In accordance with the dimensions of commercially available multiwell plates the temperature-control fingers can be arranged within an area with a length of 127.8 mm and width of 85.5 mm. The number of temperature-control fingers can correspond to the number of cavities of the multiwell plate and preferably have one of the following values: 6, 8, 12, 16, 24, 48, 96, 384 or 1536. Furthermore, it is possible for a different number of temperature-control fingers to be arranged on the base body, in particular a multiple of the aforementioned variants, in order, for example, to temperate control several multiwell plates with one temperature-control body.

The temperature-control fingers are preferably made of a material of high thermal capacity and high thermal conductivity, preferably of a metallic material. In particular, the thermal capacity of the temperature-control fingers is greater than that of a conventional commercial multiwell plate.

The base body of the temperature-control body comprises at least one line through which a cooling fluid can flow, with an inflow connection and an outflow connection for connecting the at least one line with a cooling circuit and/or a heating circuit. The line course of the at least one line is preferably of meandering or spiral shape in order to achieve a desired temperature profile evenly distributed over the base body. An advantageous variant provides that the flow of a temperature-control fluid through the at least one line can be controlled in such a way that predetermined individual temperature-control fingers and/or at least one predetermined partial group of temperature-control fingers can be temperature controlled differently compared to the remaining temperature-control fingers. This can be achieved, for example, through several fluid lines or line sections which can be switched on or switched off in order to temperature control partial groups of temperature-control finger differently.

The end faces of the temperature-control fingers can be flat or slightly curved. This configuration is advantageously suitable for the temperature-control of multiwell plates which have cavities with a flat base or a slightly curved round base.

A further variant of this embodiment is characterized by an inclination of the end faces of the temperature-control fingers in relation to a planar surface of the base body which increases from the middle to two opposite marginal areas of the temperature-control body. The increasing inclination can be formed by an increasing oblique position of the temperature-control fingers arranged on the planar upper side of the base body or an increasing bevel of the end faces of the temperature-control fingers. According to this embodiment the fact is utilized that multiwell plates are usually made of plastic, e.g. polystyrene or polyvinyl chloride, and bend easily under pressure. This bending can be advantageously utilized by an outwardly increasingly inclination of the face ends of the temperature-control fingers in order to ensure that all cavities come into planar contact with the temperature-control body.

Another alternative embodiment provides that an outer wall of the bases of the cavities and an end face of the temperature-control fingers have a complementary form-corresponding non-planar surface shape in order to create a local form fit. In other words, the end face of the temperature-control fingers is designed in accordance with the key and lock principle as a counter contour to the contour of the underside of the cavities. For example a surface shape of the end faces of the temperature-control fingers and a surface shape of the outer walls of the bases of the cavities are designed as interlocking toothing in order to create a local form fit. This alternative embodiment offers the advantage that even in the case of cavities with small diameters a large area contact between the cavity and corresponding cooling finger and thereby a comparatively large cooling surface and faster temperature controlling are made possible.

The invention also relates to an arrangement of a temperature-control body, as disclosed herein, and a multiwell plate, the grid spacing of whose cavities arranged in rows and columns corresponding to the grid spacing of the temperature-control fingers.

According to a further aspect of the invention a temperature-control apparatus for freezing samples, in particular for cryopreservation, and/or for the thawing of samples, in particular a cryopreserved sample, is provided. These samples can, in particular, be biological samples. The temperature-control apparatus comprises a temperature-control body as disclosed in this document. The temperature-control apparatus also comprises a positioning device for positioning the temperature-control body of a multiwell plate in a predetermined position relative to each other wherein the grid spacing of the cavities arranged in rows and columns corresponds to the grid spacing of the temperature-control fingers and wherein in the predetermined position the multiwell plate is positioned above the temperature-control body and the cavities are each positioned flush to the longitudinal axis of one of the temperature-control fingers. The temperature-control apparatus also comprises a device for bringing into contact the temperature-control fingers of the temperature-control body with the bases of the cavities of a multiwell plate positioned in the predetermined position.

A possible implementation provides that the device for bringing into contact comprises a pressing body which can be pressed from above onto a multiwell plate positioned above the temperature-control body in order to bring the bases of the cavities of the multiwell plate by the effect of the pressing pressure into contact with the end faces of the temperature-control fingers. The pressing body preferably comprises a contact surface with the multiwell plate of at least the same length and width as the matrix-like arrangement of the cavities of the multiwell plate.

In a further advantageous embodiment variant of the temperature-control apparatus, the device for bringing into contact comprises a plurality of electrically controllable actuators which are designed to act on the upper side of a multiwell plate positioned above the temperature-control apparatus indirectly, e.g. by way of the aforementioned pressing body, or directly, in order, on operation of the actuators, to change a relative distance between the multiwell plate and the temperature-control body so as to move the temperature-control fingers and the bases of the cavities into and/or out of contact. The electrically controllable actuators can be designed as micromechanical actuators or as piezo-electrical actuators.

It is also advantageous to design the temperature-control apparatus in such a way that the plurality of the electrically controllable actuators can be controlled by the temperature-control apparatus individually and/or in partial groups in order to bring individual cavities and/or partial groups of cavities, e. g. individual rows or columns, into and/or take them out of contact with the temperature-control body, irrespective of the other cavities. This embodiment variant again makes use of the bendability of plastic multiwell plates in that by only controlling those actuators arranged in a selected area above the multiwell plate, only those cavities in this area can be moved into and out of contact with the temperature-control body.

In contrast to cryo-microscopes in which the cooling and heating rate is controlled by temperature controlling of a cooling medium, according to the temperature-control apparatus this takes place via a preferably very rapid change in the contact of pre-temperature control body with the multiwell plate. Here, the temperature-control fingers can all at the same time or in groups, and in individual cases only one individual temperature-control finger can be pressed onto the underside of the cavities of the multiwell plate and retracted again so that a temperature bridge is produced and undone between the multiwell plate and the temperature-control fingers so that heat can also be removed from the sample or introduced into it.

A further advantage of the embodiment variant in which the electrically controllable actuators are high-precision micromechanical actuators or piezo-electric actuators, consists in the fact that such actuators can be controlled by a control unit of the device for bringing into contact in such a way that consecutive bringing into contact, taking out of contact and bringing back into contact of the multiwell plate and temperature-control body can be carried out within a time in a range of 1 ms (millisecond) to 1 s (second) and that this can be carried out with a spacing accuracy of <1 µm. According to a further aspect, by means of the electrically controllable actuators displacements of the multiwell plate in the direction of the temperature-control body in the range from 1 µm to 1 mm can be provided. Through this almost any temperature programs and temperature gradient courses can be implemented.

As has already been stated, the temperature-control apparatus is configured for handling a multiwell plate, the grid spacing of whose cavities arranged in rows and columns corresponds to the grid spacing of the temperature-control fingers of a temperature-control body of the temperature-control apparatus. Furthermore, the temperature-control apparatus can comprise such a multiwell plate.

The multiwell plate can be a commercially available multiwell plate. The multiwell plate can also differ from commercially available multiwell plates and be adapted for use for cryopreservation and for use with the temperature-control body and/or temperature-control apparatus. Within the framework of the invention there is, in particular, the possibility that integrated into the bases of each of the cavities there is an electrically controllable heating and/or cooling element, preferably a Peltier element and/or that a temperature sensor is integrated into at least one of the bases of the cavities. Furthermore, the bases of the cavities can be thin and made of a thermally conductive material or be provided with a structure on the underside which produce a greater contact surface with the temperature-control body.

The multiwell plate modified in accordance with the latter variants is also to be disclosed and claimable as a separate subject matter.

The temperature-control apparatus can also in a known manner comprise a temperature-control chamber or housing, coolable from below, which is fillable and/or is filled with a dry gas and in the cooled state has a vertical temperature layering in the temperature-control chamber with a lower cold layer and an upper warm layer, as well as at least one lock provided on a housing wall of the temperature-control chamber for introducing and removing a multiwell plate. Advantageously two such locks are provided: a first lock via which the multiwell plate is introduced in or removed from the chamber in the warm state, and a second lock via which a multiwell plate is introduced into or removed from the chamber in the cold state.

It has already been stated that the temperature-control apparatus comprises a temperature-control body according to the invention. In particular the temperature-control apparatus can comprise a first temperature-control body arranged in the lower cold layer of the temperature-control chamber and connected to a cooling circuit, for the cryopreservation of biological samples and/or a second temperature-control body, arranged in the upper warm layer and connected to a heating circuit, for thawing out cryopreserved biological samples.

According to further aspect of this variant, a multiwell plate containing at least one sample to be thawed stored in the lower cold layer of the temperature-control chamber, can be positioned above the second temperature-control body by means of the positioning device. Additionally a multiwell plate containing at least one sample to be frozen and introduced into the temperature-control chamber via the at least one lock can be positioned by means of the positioning device above the first temperature-control body. For this the positioning device can comprise a suitably designed guide mechanism for moving the multiwell plate within the temperature-control chamber. In accordance with this aspect a multiwell plate positioned above the first and/or second temperature-control body can be lowered and/or raised in a controlled or regulated manner by means of the device for bringing into contact in order to be brought into contact and/or taken out of contact with the temperature-control body.

Alternatively the positioning device can also be designed to move the temperature-control bodies towards the multiwell plate instead.

According to a further aspect, the temperature-control chamber can be cooled with liquid gases such as LN2, N2 gas or a Sterling motor. For example, in a trough at the base of the temperature-control chamber liquid nitrogen can be stored openly or introduced into a sponge-like material through which the vertical temperature layering is produced.

It is also advantageous to arrange an ice trap in the temperature-control chamber in order to force ice formation via the ice trap if humid air should penetrate from outside into the temperature-control chamber through the introduction or removal of a multiwell plate.

According to another aspect, the vertical temperature gradient within the temperature-control chamber is set so that the warm layer has a temperature which essentially corresponds with a predetermined starting temperature of a freezing process or a predetermined target temperature of a thawing process, whereas the cold layer has a temperature which essentially corresponds with a predetermined target temperature of the freezing process or a predetermined starting temperature of the thawing process.

A further aspect of the invention relates to a method of freezing biological samples, in particular for cryopreservation, and/or thawing of biological samples, in particular cryopreserved samples, using a temperature-control body as disclosed in this document and/or a temperature-control apparatus as disclosed in this document.

According to a preferred embodiment, the method comprises the application of a substance onto a sample stored in a cavity of the multiwell plate.

In accordance with an advantageous variant, the applied substance is a solution which on hardening closes off the surface of the cavity contents from the outside, preferably in a gas-tight manner so that no cover or similar is required as a closure. The substance can be a natural or synthetic oil, a liquid or a gel which cannot be mixed with an aqueous solution, or is solid $CO_2$.

According to a particularly advantageous variant, the substance is applied to the already frozen sample wherein after and/or during thawing of the sample the substance brings about a predetermined reaction or interaction with the sample. Preferably, a substance is used from the condition of which it can be derived whether after freezing of the sample thawing has taken place in the meantime.

According to a further advantageous variant, the substance has a higher density than that of the nutrient solution surrounding the sample, so that after thawing the order of the sample and the substance reverses, so that, for example, cells floating in a nutrient solution can be simply removed.

According to a further advantageous variant, a substance is applied, wherein from the condition of the applied substance information about the sample can be derived and/or on thawing of the sample the substance brings about a predetermined reaction or interaction with the sample. For example fluids can also be added which on freezing produce a particular pattern or have a temperature sensor function by means of which it can be seen whether thawing has taken place in the meantime and the structure, color, mixture etc. has been changed. This can involve re-crystallization processes which are not macroscopically visible, but can be easily recognized and quantified via scattered light measurements, fluorescence measurements, Raman measurements or similar. For example, the substance can be a dilution or washing solution or an cryoprotection agent, act on the sample as a differentiation factor in relation to the sample or be a substance which contains antioxidants, anti-apoptosis substances or live/dead staining agents.

It is emphasized that the above procedural aspects relating to the application of the substance to a sample stored in the cavity is also possible independently of the use of the temperature-control apparatus and/or the temperature-control body and can therefore also be claimed independently of the use of the temperature-control apparatus and/or the temperature-control body.

In order to avoid repetitions features disclosed purely in accordance with the device also apply as disclosed and claimable within the framework of the manufacturing method.

In summary, with the present invention multiwell plates can be used directly for cryopreservation so that each transfer into new receptacles can be dispensed with. In principle, through adapting the temperature-control body to the format of the respectively used multiwell plate, multiwell plates with any number of cavities can be used directly for cryopreservation. As a result, known cryotechnologies can be efficiently included in the existing high throughput process chains so that the automation chain of multiwell plate-base device platforms is closed in the cryo sector too.

BRIEF DESCRIPTION OF SEVERAL VIEWS OF THE DRAWINGS

Further details and advantages of the invention will be described below with reference to the attached drawings. In these show.

DETAILED DESCRIPTION OF PREFERRED EMBODIMENTS

Equal components are given the same reference numbers in the figures.

Figure 1:
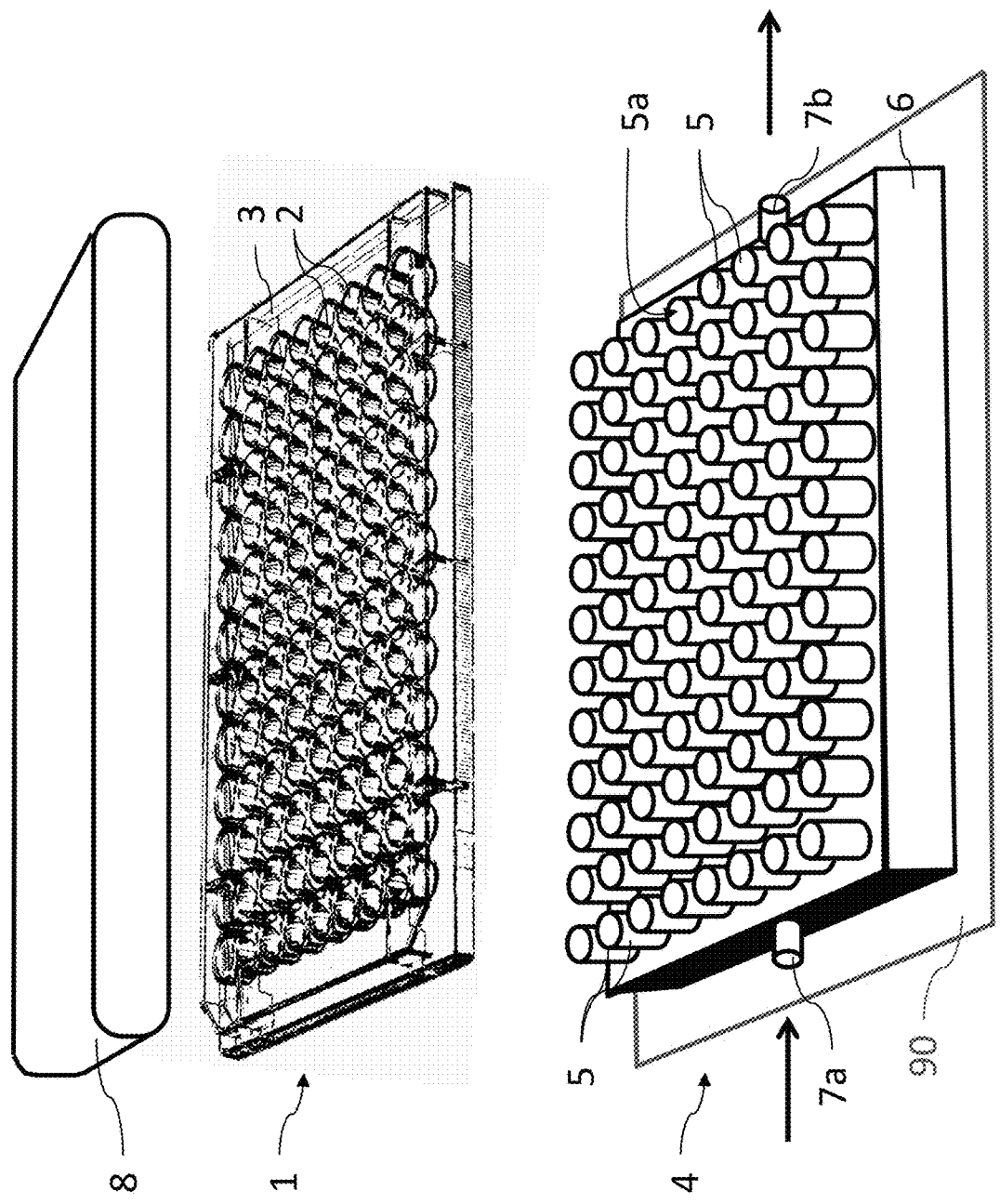
FIG. 1 a perspective view of a multiwell plate and a temperature-control body according to an embodiment of the invention.

FIG. 1 shows a perspective view of a multiwell plate 1 and a first embodiment of the temperature-control body 4 according to the invention. In the middle a schematic oblique view shows a commercially available plastic multiwell plate 1 in the standardized 96 well format. According to the standard the cavities (wells) 2 are arranged next to each other in a matrix-like manner in eight rows of twelve cavities each and constitute recesses for accommodating the sample(s) on such a multiwell plate 1. In accordance with the standard ANSI/SBS 4-2004 the grid spacing of adjacent cavities in a 96 well format multiwell plate is 9 mm.

Such multiwell plates 1 can be covered with a plastic cover, which can also be left out in the case of machines for filling, emptying or other manipulations. On the underside the cavities 2 are closed off in a planar manner with a thin plastic sheet or film which in terms of its optical quality generally allows microscope images of adhered cells.

Shown underneath the multiwell plate 1 in FIG. 1 is an example temperature-control body 4 for the multiwell plate 1. The temperature-control body 4 comprises a cuboid base body 6 through which a temperature-control fluid can flow and a plurality of protruding cylinder-shaped temperature-control fingers 5 arranged in rows and columns on an upper side of the base body 6 exactly matching the pattern of the 96-well multiwell plate 1. The temperature-control body 4 is made of a material with a high thermal capacity and good thermal conductivity. As a rule, metals such as silver or alloys are used.

Corresponding to the multiwell plate 1, 96 temperature-control fingers 5 are thus also arranged in eight rows of twelve temperature-control fingers 5 each in a matrix-like manner. The grid spacing of the temperature-control fingers 5 thus corresponds to a grid spacing of the cavities 2 of the multiwell plate 1, i.e. the distance between adjacent temperature-control fingers correspond to the spacing between adjacent cavities and in this case is thus also 9 mm. The temperature-control fingers 5 are each essentially identically formed and regularly arranged essentially equidistantly in area directions at right angles to each other spanning the contact surface with the multiwell plate 1. The temperature-control finger 5 can be provided in one piece with the base body 6. The temperature-control fingers 5 are in very good, generally thermal contact with the temperature-control bodies 6 arranged underneath.

Via at least 2 openings 7a, 7b a temperature-control gas or a temperature-control liquid can flow through the base body 6.

For this in the temperature-control body 6 a meandering or spiral course of a fluid guide connecting the two openings is provided so that an even or desired temperature profile is achieved, via which the temperature-control fingers each assume the temperatures prevailing at their location.

The temperature-control fingers 5 have as high a thermal capacity as possible which is much greater than that of the base areas of the multiwell plates so that during bringing into contact they dominate and determine the temperature of the cavity area with the biological sample, i.e. cooling and heating are essentially now only limited by the thermal conductivity of the base areas of the multiwell plate 1 and the biological sample.

For cooling and/or heating biological samples which are stored in a multiwell plate with a different format, for example in a multiwell plate with 8, 12, 16, 24, 48, 96, 384 or 1536 cavities a temperature-control body appropriately adapted to this format can be used, which then has 8, 12, 16, 24, 48, 96, 384 or 1536 temperature-control fingers 5, the grid spacing of which is matched to the grid spacing of the multiwell plate.

The principle of cooling a 96-well multiwell plate 1 from room temperature to a target temperature of, for example, −150° C. will be explained below by way of the example of identical cooling of all 96 cavities 2. Through different temperature controlling of the rows or columns of the temperature-control fingers or via heating elements (not shown) in the temperature-control fingers 5 different temperatures can also be brought about on the individual temperature-control fingers 5.

For freezing of a 96-well multiwell plate 1, it is initially brought to a temperature of between 1° C. and 15° C. at which the cryoprotection medium is added from above via pipettes. In the meantime the temperature-control body 4 has been brought to the target temperature by way of passing though nitrogen gas at a temperature of −150° C. to −195° C. so that all the temperature-control fingers 5 also assume this temperature. By means of a mechanism described below in the context of FIG. 4 the 96-well multiwell plate 1 is pressed now from above onto the temperature-control body 4 by a flat pressing body 8 so that the end faces 5a of the temperature-control fingers 5 come into direct material contact with the individual bases of the 96 cavities 2 of the multiwell plate 1. Instead of the pressing body 8 a piezo-controlled device can also be used for bringing the temperature-control fingers 5 into contact with the bases of the cavities 2 (shown in FIG. 3), which allows the contact of the multiwell substrate with the temperature-control fingers 5 to open and close again through perpendicular movement. For this only small gaps in the micrometer range are required. Through multiple repetition, solely in this way a temperature profile of the entire plate can be run.

Additionally or alternatively the temperature of the gas flow through the base body 6 can be altered, through which slower T profiles can be run as is also usual in the cryo-preservation of cells (for example in the region of several fractions ° C. per minute, a few ° C. per minute). In the case of heating the procedure is reversed: The multiwell plate 1 is very quickly brought into contact with a temperature-control body 4 heated to a high temperature. A warm or a hot gas or also a corresponding liquid can flow through this, the temperature of which in the simplest case corresponds to the target temperature of, for example 10° C. at which the cryprotection medium can be washed out, or directly to 37° C. Here the multiwell plate 1 is also pressed rapidly to the temperature-control body 4.

For extremely rapid heating as required in the case of stem cells and in particular IPS, the temperature control body 4 is brought to 40° C. to 300° C. and is only brought into thermal contact with the multiwell plate 1 until the target temperature is reached. Via opening and closing the thermal contact between the temperature-control fingers 5 and the cavities 2 the courses of the temperature during heating can also be controlled.

Figure 2:
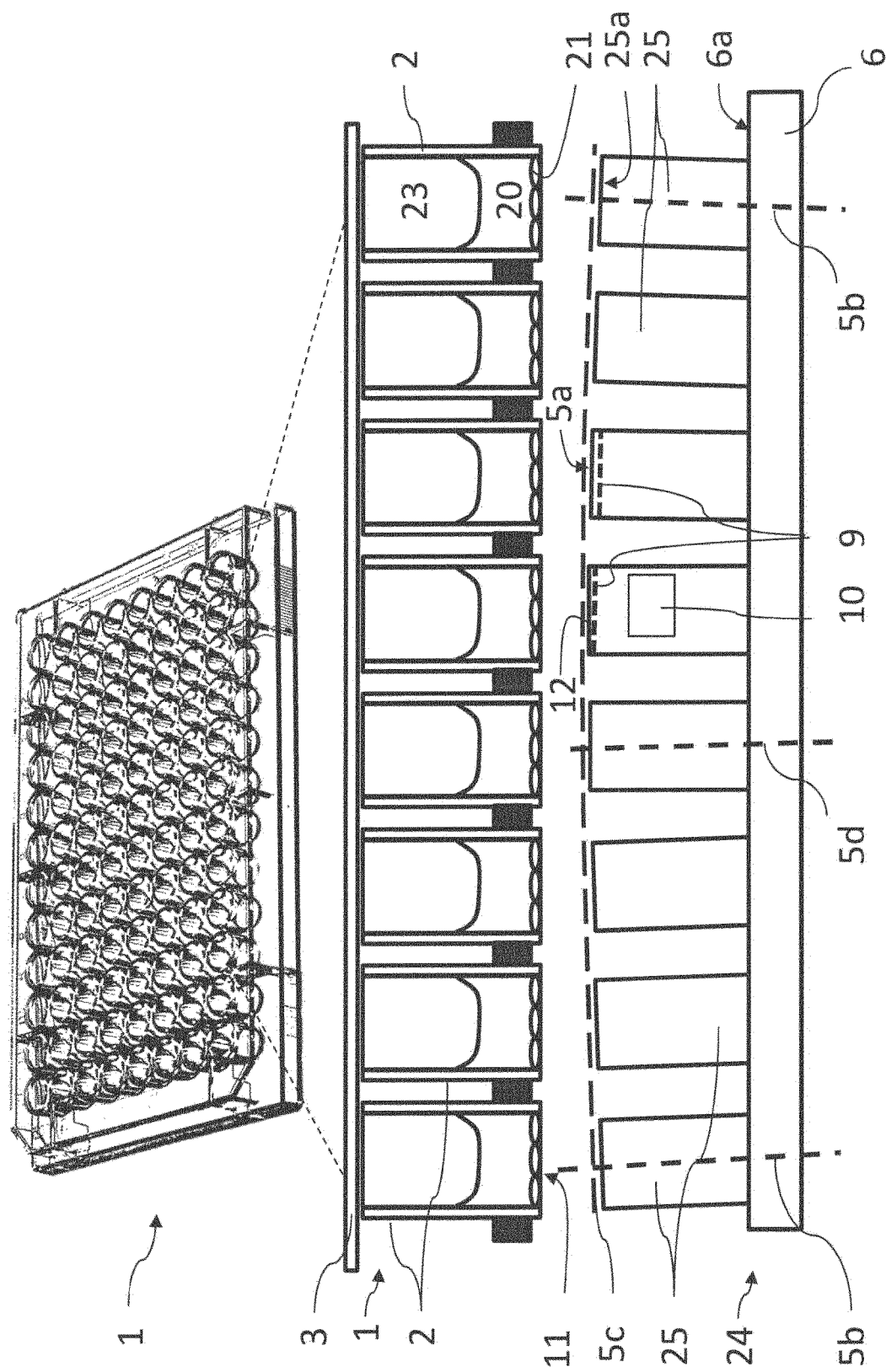
FIG. 2 an arrangement of a multiwell plate and a temperature-control body from which a section is enlarged and shown in cross-section.

In the lower section FIG. 2 shows a cross-section of a temperature-control body 24 which has a base body 6 through which a temperature-control fluid can flow and a plurality of protruding temperature-control fingers 25 arranged in rows and columns on an upper side of the base body 6. The grid spacing of the temperature-control fingers 25 again corresponds to the grid spacing of the cavities 2 of the multiwell plate 1, which in the middle of FIG. 2 is partially shown enlarged and in cross-section. Shown above it is the multiwell plate 1 in an oblique view with the marked area used as the cross-section shown.

In each of the cavities 2 there is a gas space 23 at the top and the biological sample 20 with adhered cells 21 on the upper side of the base plate 11 of the cavities 2. In the embodiment the multiwell plate 1 is still covered with a cover 3.

In order to achieve good pressing and thereby thermal contact between the temperature-control body 24 and the multiwell plate 1, in this variant of embodiment the temperature-control fingers 25 are not perpendicularly upright on the surface 6a of the base body 6 but are increasingly inclined towards the edges of the multiwell plate 1. This is shown in the figure in an exaggerated manner by the dashed line 5c and the two longitudinal axes 5b of temperature-control fingers 25 arranged in the outer area, which in comparison with the longitudinal axis 5d of a centrally arranged temperature-control finger 25 are tilted outward. Through the flat pressure from above or below the multiwell plate 1 is bent slightly in a lens-shape manner, which ensures that with their base sides 11 all the cavities 2 come into equally good planar contact with the temperature-control fingers 25. The upper surface of the temperature-control fingers, in particular the end face 25a can, as illustrated by an example cylinder in FIG. 2, be covered with a well thermally-conducting layer 9 through which very rapid cooling and heating become possible. Heating/cooling elements 10 can additionally be integrated into the temperature-control fingers 25 via which the temperature of individual elements can be controlled. To this end, near or on the end face of the temperature-control fingers 25 temperature sensor 12 are provided, for example with a flat configuration of a platinum resistance temperature sensor, such as a PT 100 or PT 1000 sensor. To simplify the illustration the aforementioned temperature sensors 12, the layer 9 of higher thermal conductivity or the heating/cooling elements 10 are only shown schematically for one or two temperature-control fingers 25, but can be provided on all temperature-control fingers 25.

Figure 3:
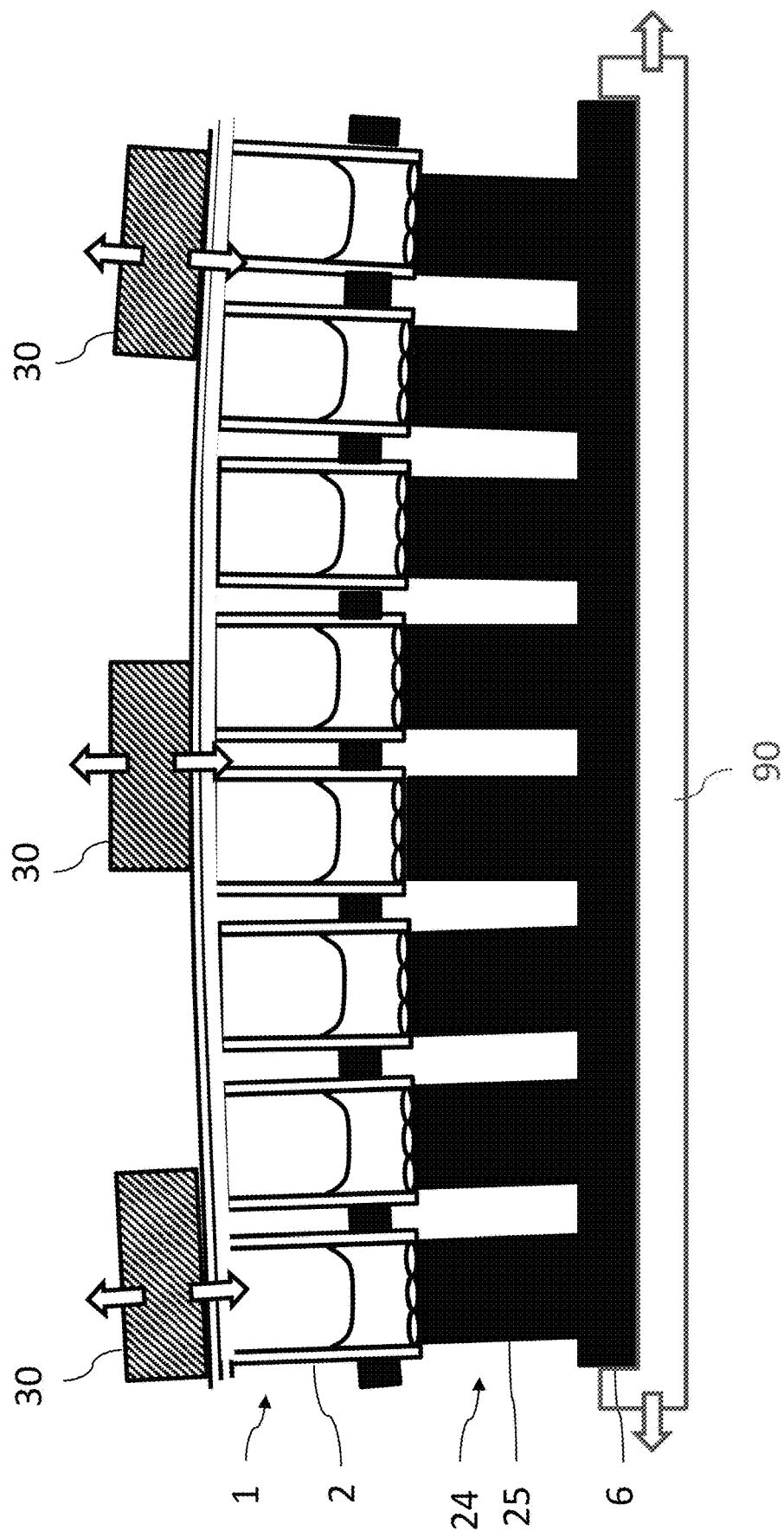
FIG. 3 a cross-sectional view of a multiwell plate and a temperature-control body according to another embodiment of the invention.

In analogy to FIG. 2, FIG. 3 shows a cross-section of a multiwell plate 1 which is in contact with the temperature-control body 24. The special feature of this embodiment is that piezo-electric actuators 30 are firmly arranged on the cover of the multiwell plate 1 so that by way of expansion or shrinkage of the piezo-electric actuators 30 (shown by the arrows) contact between the cavities 2 and the temperature-control fingers 25 can be established or interrupted. This involves movements in the range from 1 to several 100 µm.

Figure 4:
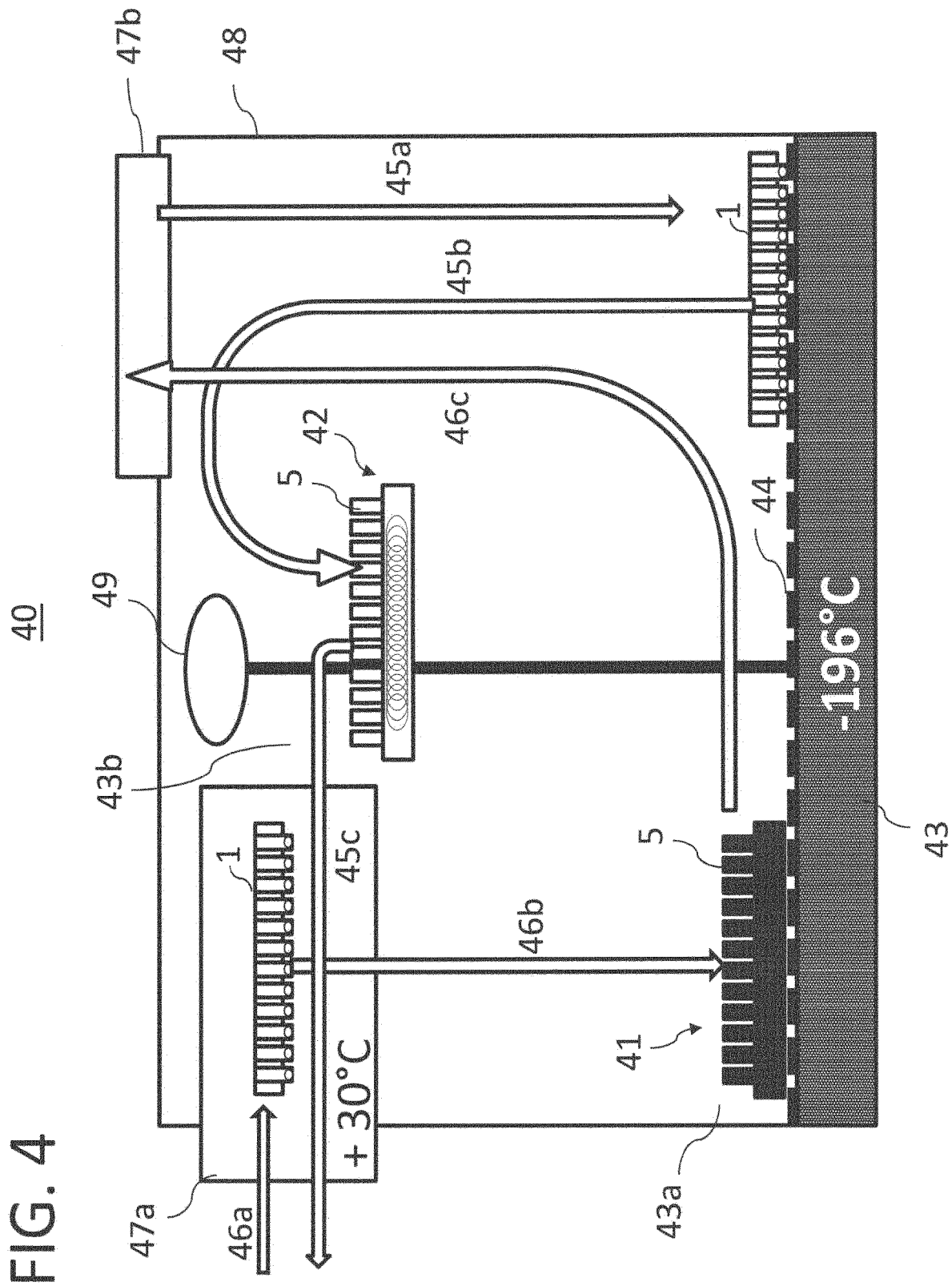
FIG. 4 schematically a temperature-control apparatus and temperature-control method according to an embodiment of the invention.

FIG. 4 shows as an example of a temperature-control apparatus 40 for the automated and direct cryopreservation of biological samples stored in the multiwell plates 1. The apparatus 40 comprises a temperature-controlled chamber 48 in which there is no moisture so that no relative humidity of the air can precipitate as ice. The chamber 48 also has areas which are at least at the initial temperature of the multiwell plate as well as at the required target temperature.

At the base of the temperature-control chamber 48 there is a trough 43 containing liquid nitrogen (LN2) openly or in a sponge-like materials, e.g. steel wool, porous aluminum etc. This is covered with a perforated metal sheet 44 which is intended to prevent parts falling into the nitrogen pool with a temperature of −196° C.

By the evaporation of the LN2 a dry nitrogen atmosphere is produced in the interior which is structured in horizontal layers in such a way that an almost linear T-gradient with a lower cold layer 43a at around −196° C. and an upper warm layer 43b at around 10° C. or warmer is formed.

In addition two locks 47a and 47b are shown which are arranged on the housing wall of the temperature-control chamber 48. Via the lock 47a a multiwell plate 1 is introduced into the temperature-control chamber 48 or removed when warm. Via the lock 47b a multiwell plate 1 can be introduced into the temperature-control chamber 48 or removed when cold.

If humid air penetrates into the temperature-control chamber 48 through introducing or removing a multiwell plate 1, ice formation is forcible brought about by means of an ice trap 49. This is a cooled body in the warm area 43b. In order not to bring in humidity via the procedures, a hood (not shown) can again be placed on top of the temperature-control chamber 48 and over the locks 47a, 47b via which the gaseous dry nitrogen escapes. The entire system 40 is not closed in a pressure-right matter but has a syphon-like outlet pipe (not shown here) at the top.

In the temperature-control chamber 28 there is a fixed first cooled temperature-control body 41 for cooling introduced biological samples or the multiwell plate 1 and a second heated temperature-control body 42 for heating the biological samples or multiwell plates. Both do not have to be designed identically. Thus, for example, the surface of the end faces of the heating temperature unit 42 can be adapted to the shrunken multiwell substrate geometry at −150° C., i.e. the surface of the end faces of the temperature-control body 42 for heating can be slightly smaller than the end faces of the temperature-control body 41 for cooling.

The device 40 also comprises a positioning device 90 (FIGS. 1 & 3) by means of which the multiwell plates 1 to be temperature-controlled can be moved within the chamber 49 in accordance with the displacement paths illustrated by the arrows 45a-c or by the arrows 46a-c and by means of which the multiwell plates can, in particular, be positioned in a precisely aligned manner above the temperature-control bodies 41 and 42. The arrows 45a-c show the temporal and spatial sequence when heating a cryogenic multiwell plate 1. The arrows 46a-c illustrate the sequence when cooling a multiwell plate 1. The paths indicated by the arrows are traversed by mechanical elements of the positioning device 90, the drives of which are preferably located outside the temperature-control chamber 48, and the multiwell plates 1 are moved by means of a conventional guide system, for examples rods, coils etc. (not shown).

For example, a multiwell plate 1 containing biological samples to be frozen is introduced into the temperature-control chamber 48 via the lock 47*a* (arrow 46*a*) and by means of the positioning device is moved into the cold layer 46*a* and there positioned above the first temperature-control body 41 standing on the perforated plate 44 (arrow 46*b*).

Positioning takes place in such a way that the cavities of the multiwell plate 1 are each positioned in alignment with the longitudinal axis of one of the temperature-control fingers of the temperature-control body 41. Subsequently the thus positioned multiwell plate is lowered in a controlled or regulated manner by means of a device for bringing into contact (not shown), such as described above in connection with FIG. 3, in order to be brought into contact with the temperature-control body 41.

After reaching the target temperature, the multiwell plate 1 can either be placed for storage in the lower cold layer 43*a* or removed for further processing from the temperature-control chamber 48 via the second lock 47*a* (arrow 46*c*).

Figure 5:
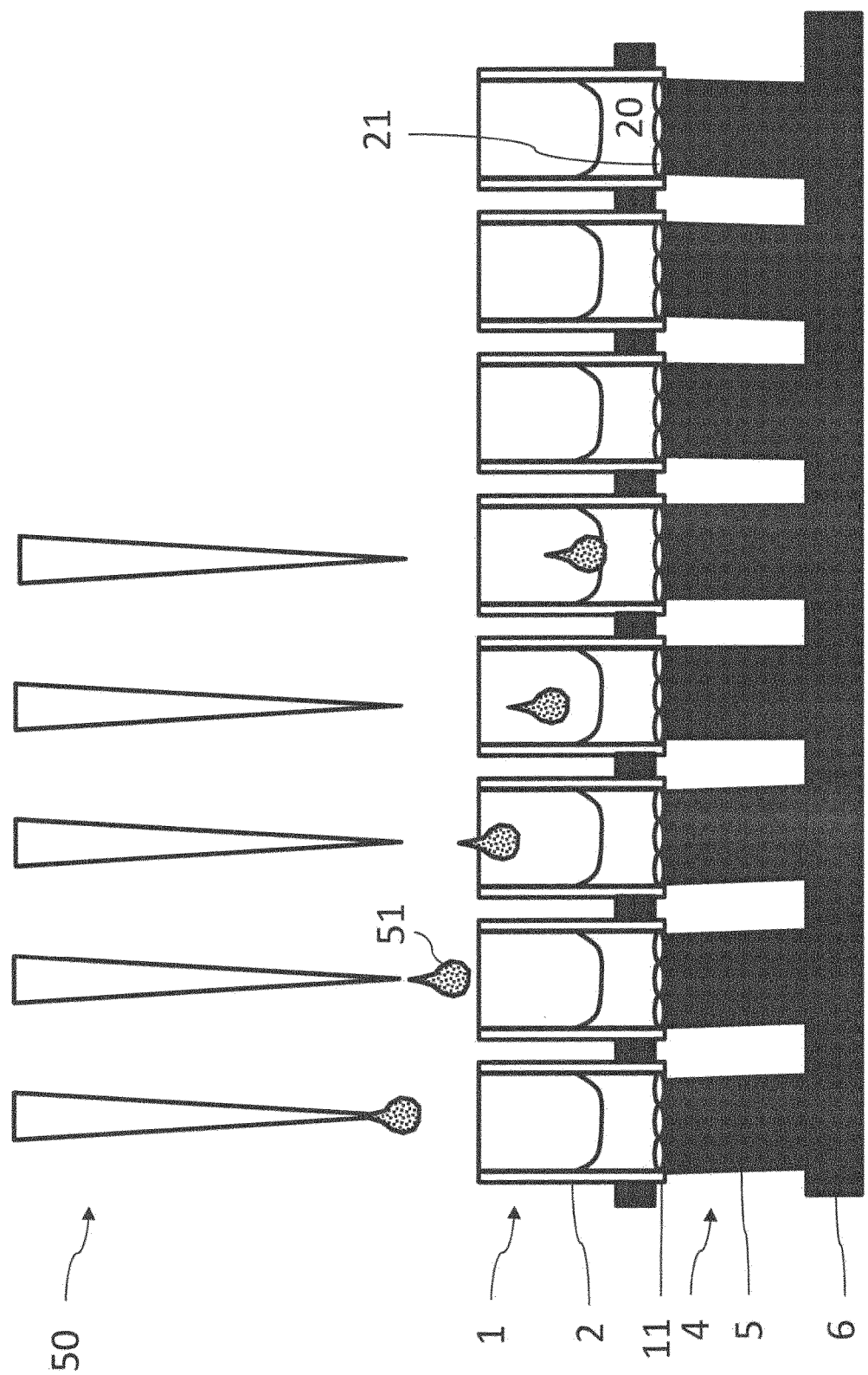
FIG. 5 schematically the application of a substance in accordance with an embodiment of the method.

FIG. 5 schematically illustrates the application of a substance on the biological samples stored in the cavities 2 and for this shows a row of cavities 2 with a fluid filling 20 and cells 21 on the cavity bases 11. In the row of cavities 2 the base plates 11 are in thermal contact with the temperature-control fingers 5. Before, during cooling or heating as well as afterwards in the frozen or thawed state, other substances 51 are added to the cavities 2 with a pipetting device 50, e.g. with a pipetting robot. For example, these can be cryoprotection agents, particle suspensions, solidifying gels and similar, which are useful during freezing, but can also be closing material which on solidification closes off the surface of the actual cavity contents from the outside so that no cover or other object is required as a closure, which simplifies the automation processes. However, fluids can also be added which on freezing produce a particular pattern or have a temperature sensor function by means of which it can be seen whether thawing has taken place in the meantime and the structure, color, mixture etc. has been changed. This can involve re-crystallization processes which are not macroscopically visible, but can be easily recognized and quantified via scattered light measurements, fluorescence measurements, Raman measurements or similar.

Of particular importance is the application of substances in solid or liquid form into the cavities 2 if their content 20 is already frozen. These could be differentiation factors for stem cells, which become active immediately after thawing, protective materials or genetic material which only combine with the solution below it after thawing out. They can also be dilution media which after thawing out reduce the concentration of the anti-freeze agents.

Figure 6A:
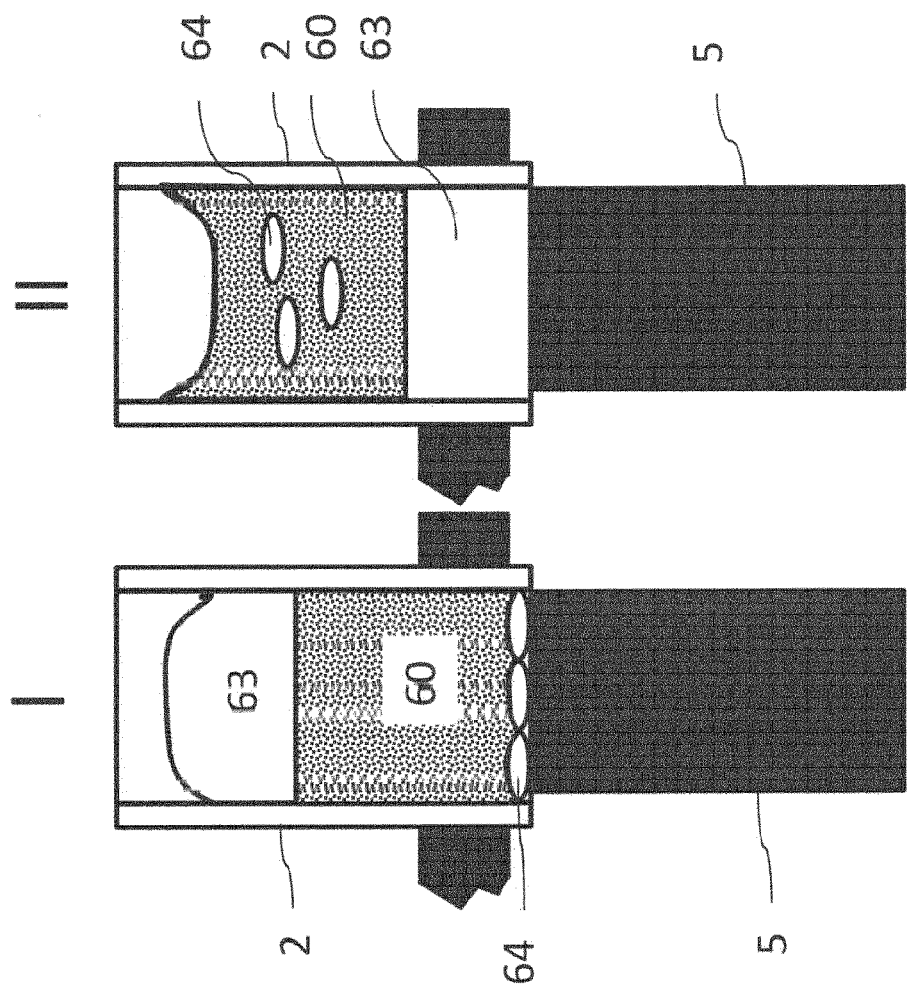
FIGS. 6A and 6B a unit comprising a temperature-control finger and filled cavity.

FIG. 6A shows an arrangement of a temperature-control finger 5 and a cavity 2. In the cavity 2 there is a filling consisting of three materials. At the bottom on the base is the culture medium 60 in which the biological samples (here shown as cells on the base plate) are located, above this is a medium 61 which is applied after freezing of the medium 60 so that it does not mix with it. This is all covered with a further medium 62 which produces a gas-tight closure with regard to the outside atmosphere. The medium 62 can be a natural or synthetic oil, a fluid that cannot be mixed with aqueous solutions, a gel or also solid CO2. The advantage of such arrangements is that they can be optimally adapted to the thawing process or deep-freezing. The nature and arrangement of the media determine the reaction when thawing out. Staggered liquefaction therefore takes place at different temperatures. Depending on the composition of the filling, media can be displaced in such a way that a new sequence comes about, as shown in FIG. 6B.

Figure 6B:
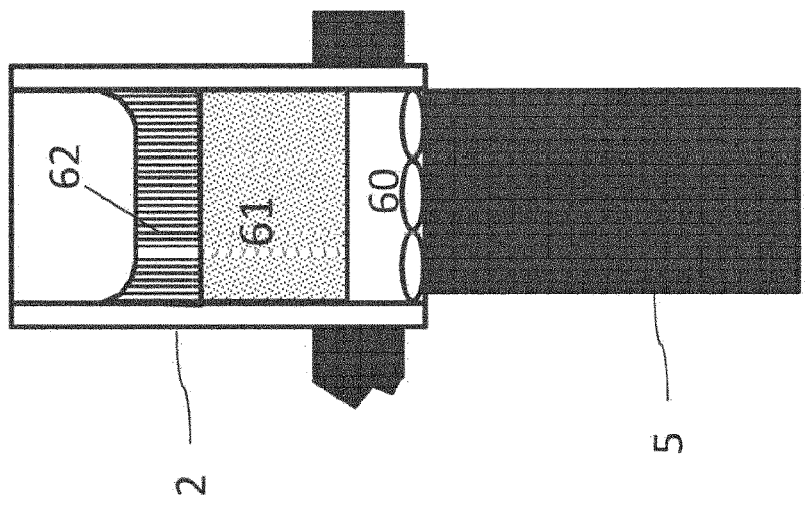

FIG. 6B shows two different states of an arrangement of a temperature-control finger 5 and a cavity 2. In the first state, designated "I" the arrangement is shown in the cold state in which nutrient medium 60 is frozen, whereas in the second state, designated "II" the arrangement is shown in the warm state in which the nutrient medium 60 is thawed out. For example, if in the frozen state a silicone oil 63 is applied to the solid nutrient medium, which has a higher density than the nutrient solution 60, the sequence of this layering will change around after both phases become liquid on increasing the temperature. As during thawing cells 64 easily detach from the surface and pass into suspension, after thawing they float in the nutrient solution 60 which rises and ultimately becomes the upper layer, which in automatic systems can be very easily removed and without having to take off a cover.

Alternative variants can be developed for freezing, in that, for example, glycerin solutions are used which remain liquid at temperatures down to −40° C. or do not take on a solid state at all. A particular advantage of this arrangement and method is the possibility of monitoring the observed cryogenic storage of samples and combination of materials in a solid and liquid state which is not possible at normal temperature.

Figure 7A:
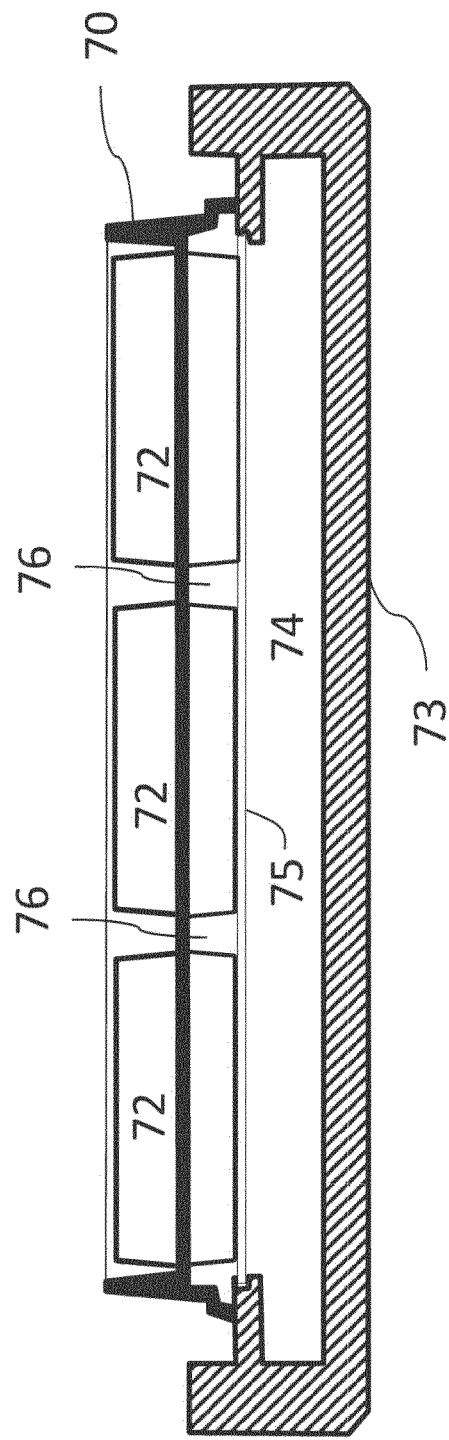
FIGS. 7A and 7B a cross-sectional view of a multiwell plate on a temperature-control body according to another embodiment.
Figure 7B:
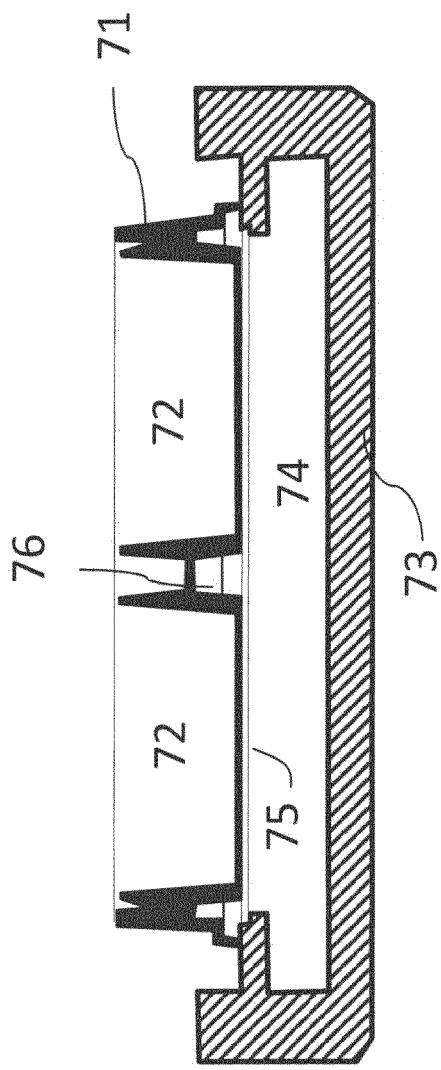

FIGS. 7A and 7B show two classic well plates 70, 71 with larger cavities 72 with a diameter of approximately 2 to 3 cm. The well plates 70, 71 are designed as an injection-molded component in a form modified for freezing the multiwell plate in its entirety. The base plate 75 comprises a thin material that conducts heat well, e.g. a polymer, a metal, a metal coating or also diamond, so that the heat can be easily removed and introduced via the cooling and warming space 74 located in a stable cooling or warming body 73. The well plates 70, 71 are pressed from above onto the temperature-control unit 72 and through the generation of a slight negative pressure over the hollow spaces 76 can be bent in the well plate. This variant of overall cooling of the multiwell substrates is a simplified form which can be combined with the temperature-control body variants according to FIGS. 1 to 6. The introduction of the temperature-control body 4, 24 into the space 74 is one such combination possibility. A cooling or heating fluid or the temperature-control gas flows through this space, wherein the corresponding temperature courses are transferred via the multiwell substrate base 75 into the cavities 72. In all variants temperature sensors can in be integrated, e.g. in the form of flat Pt-100 or Pt-1000 sensors which are arranged on the base plate 75 or in each cavity 72. Alternatively, a temperature sensor can be arranged in a reference cavity with a similar or identical filling which provides the regulating values for control the temperature courses.

Figure 8A:
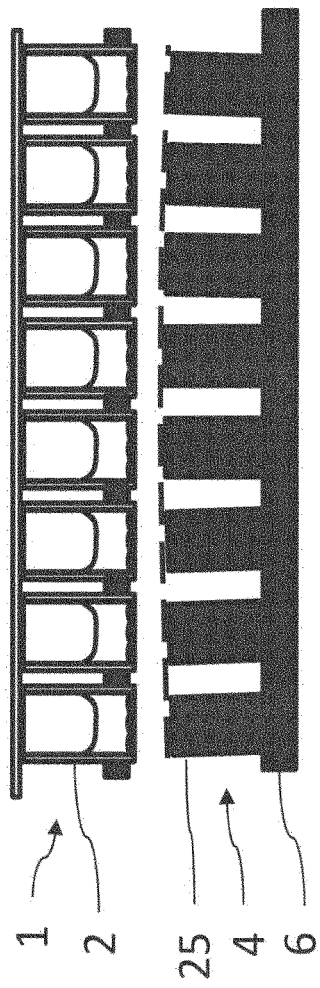
FIGS. 8A and 8B a cross-sectional view of a multiwell plate according to another embodiment.
Figure 8B:
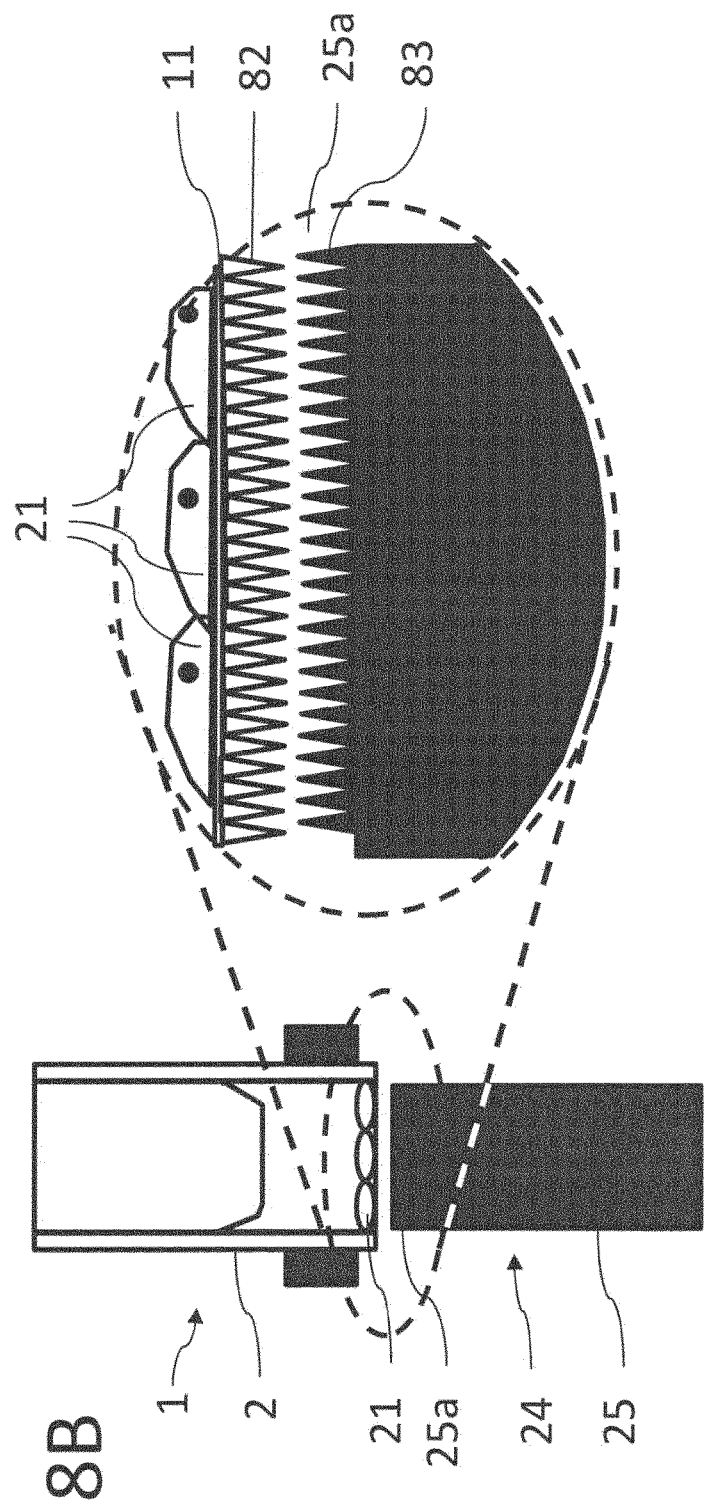

FIGS. 8A and 8B show a cross-section through a multiwell plate and a temperature-control body according to a further embodiment. Here, FIG. 8A shows a cross-section of an arrangement of a multiwell plate 1 and a temperature-control body 4, both of which are not in contact with each other yet. Shown in FIG. 8B is an individual cavity 2 with the temperature-control cylinder 25 below it. Characterized by the dashed lines in FIG. 8B a greatly enlarged excerpt of the cavity base area with the cells 21 can be seen. The cooling contact can now be considerably increased for more rapid temperature gradient processes in that the topography of the layer 82 located on the base plate 11 of the cavities 2 is designed with a counter-piece on the temperature-control body on the basis of the key and lock principle. In other words, the end faces 25*a* of the temperature-control cylinder 25 and the lower base side 11 of the cavities 2 each have a non-planar surface form 82, 83 corresponding in shape to each other in order to bring about a local form fit. The shown tip topography is only one example possibility.

Although the invention has been described with reference to certain examples of embodiment, for a person skilled in the art it is evident that different modifications can be carried out and equivalents used as substitutes without leaving the scope of the invention. Additionally, many modifications can be carried out without departing from the relevant area. Consequently the invention is not to be restricted to the disclosed examples of embodiment, but should cover all examples of embodiment which come under the scope of the attached patent claims. In particular, the invention also claims protection for the subject matter and the features of the sub-claims irrespective of the claims to which reference has been made.

The invention claimed is:

1. A temperature-control apparatus for at least freezing biological samples for cryopreservation and thawing of cryopreserved biological samples, comprising:
    first and second temperature-control bodies, each temperature-control body configured to be combined with a multiwell plate having a plurality of cavities arranged in rows and columns for at least one of freezing and thawing biological samples;
    wherein each temperature-control body comprises a base body through which a temperature-control fluid can flow; and a plurality of protruding temperature-control fingers arranged in rows and columns on an upper side of the base body, wherein a grid spacing of the temperature-control fingers corresponds to a grid spacing of the cavities of the multi well plate;
    a positioning device including guide system and drives for positioning the multiwell plate and one of the first and second temperature-control bodies in a predetermined position relative to each other,
    wherein in the predetermined position the multiwell plate is positioned above the one of the first and second temperature-control bodies and the cavities are each positioned flush to a longitudinal axis of a respective corresponding one of the temperature-control fingers; and
    a device for bringing the temperature-control fingers of the one of the first and second temperature-control bodies into contact with respective bases of the cavities of the multiwell plate positioned in the predetermined position;
    a temperature-control chamber, coolable from below, which is fillable or is filled with a dry gas and in a cooled state has a vertical temperature layering thereinside with a lower cold layer and an upper warm layer;
    at least one load-lock provided on a housing wall of the temperature-control chamber for at least one of introducing and removing the multiwell plate; and
    the first temperature-control body arranged in the lower cold layer and connected to a cooling circuit, for the cryopreservation of biological samples, and the second temperature-control body arranged in the upper warm layer and connected to a heating circuit, for thawing out cryopreserved biological samples.

2. The temperature-control apparatus according to claim 1, wherein at least one of an electrically controllable heating and an electrically controllable cooling element is integrated into at least some of the temperature-control fingers.

3. The temperature-control apparatus according to claim 1, wherein a temperature sensor is integrated in a face area of at least one of the temperature-control fingers.

4. The temperature-control apparatus according to claim 1, wherein end faces of the temperature-control fingers have at least one of the features
    (a) the end faces form flat support surfaces for bases of the cavities of the multiwell plate; and
    (b) the end faces comprise a coating of graphite or diamond.

5. The temperature-control apparatus according to claim 1, wherein the temperature-control fingers have at least one of the features
    (a) the temperature-control fingers can be arranged within an area with a length of 127.8 mm and width of 85.5 mm; and
    (b) the number of temperature-control fingers corresponds to the number of cavities of the multiwell plate.

6. The temperature-control apparatus according to claim 5, wherein the number of temperature-control fingers has one of the following values: 6, 8, 12, 16, 24, 48, 96, 384 or 1536.

7. The temperature-control apparatus according to claim 1, having at least one of the features
    (a) an outer wall of bases of the cavities and an end face of the temperature-control fingers in order to form a local form fit each comprise a non-planar surface form complementary in shape to each other; and
    (b) a surface form of end faces of the temperature-control fingers and outer walls of the bases of the cavities are designed as interlocking toothing in order to form a local form fit.

8. The temperature-control apparatus according to claim 1, one of the first and second temperature-control bodies including a base body having a planar surface, the one of the first and second temperature-control bodies having end faces with an inclination in relation to the planar surface of the base body which increases from a middle to two opposite marginal areas of the temperature-control body.

9. The temperature-control apparatus according to claim 8, wherein the inclination is formed by an increasing oblique position of the temperature-control fingers arranged on the upper side of the base body or an increasing bevel of the end faces of the temperature-control fingers.

10. The temperature-control apparatus according to claim 1, wherein integrated in the base body is at least one line, through which a temperature-control fluid can flow, with an inflow connection and an outflow connection for connecting at least one line with at least one of a cooling circuit and a heating circuit wherein the flow of the temperature-control fluid through the at least one line is controllable in such a way that predetermined, at least one of individual temperature-control fingers and at least one predetermined partial group of temperature-control fingers can be temperature controlled differently in relation to the remaining temperature-control fingers.

11. The temperature-control apparatus according to claim 1, wherein the device for bringing into contact comprises a pressing body which can be pressed from above onto the multiwell plate positioned above the one of the temperature-control bodies in order to bring the bases of the cavities of the multiwell plate into contact with end faces of the temperature-control fingers.

12. The temperature-control apparatus according to claim 1, wherein the device for bringing into contact comprises a plurality of electrically controllable actuators which are designed to act directly or indirectly on an upper side of the multiwell plate positioned above the one of the temperature-control bodies, in order, on controlling of the actuators to change a relative distance between the multiwell plate and the one of the temperature-control bodies so as to move the temperature-control fingers and the bases of the cavities into contact or out of contact.

13. The temperature-control apparatus according to claim 12, wherein the electrically controllable actuators have at least one of the features
    (a) the electrically controllable actuators are designed as micromechanical actuators or as piezo-electrical actuators;
    (b) the plurality of the electrically controllable actuators can be controlled by the temperature-control apparatus at least one of individually and in groups in order to bring at least one of individual cavities and partial groups of cavities into or out of contact with the one of the temperature-control bodies, irrespective of the other cavities;
    (c) by use of the electrically controllable actuators a displacement of the multiwell plate in the direction of the one of the temperature-control bodies in the range of 1 µm to 1 mm can be produced; and
    (d) the electrically controllable actuators can be controlled by a control unit of the device for bringing into contact in such a way that consecutive bringing into contact, taking out of contact and bringing back into contact of the multiwell plate and the one of the temperature-control bodies can be carried out within a time in a range of 1 ms (millisecond) to 1 s (second).

14. The temperature-control apparatus according to claim 1, comprising the multiwell plate, the grid spacing of whose cavities arranged in rows and columns corresponds to the grid spacing of the temperature-control fingers.

15. The temperature-control apparatus according to claim 14, having at least one of the features
    (a) integrated into the bases of each of the cavities is at least one of an electrically controllable heating and an electrically controllable cooling element;
    (b) in a least one of the bases of the cavities a temperature sensor is integrated; and
    (c) the bases of the cavities are designed to be thermally conductive.

16. The temperature-control apparatus according to claim 1, comprising
    (a) a multiwell plate containing samples to be thawed that can be positioned by use of the positioning device above the second temperature-control body; and
    (b) a multiwell plate containing samples to be frozen and introduced into the temperature-control chamber via the at least one load-lock that can be positioned by use of the positioning device above the first temperature-control body; and
    (c) a multiwell plate positioned above at least one of the first and second temperature-control bodies that can be at least one of lowered and raised in a controlled or regulated manner by use of the device for bringing into contact in order to be brought into contact or taken out of contact with the at least one of the first and second temperature-control bodies.

17. The temperature-control apparatus according to claim 14, having at least one of the features
    (a) the temperature-control chamber is cooled with liquid nitrogen (LN2), nitrogen (N2) gas or a Sterling motor;
    (b) an ice trap is arranged in the temperature-control chamber; and
    (c) the warm layer has a temperature gradient which corresponds with a predetermined starting temperature of a freezing process or a predetermined target temperature of a thawing process, whereas the cold layer has a temperature which corresponds with a predetermined target temperature of the freezing process or a predetermined starting temperature of the thawing process.

18. A method of freezing biological samples comprising freezing biological samples with the temperature-control apparatus according to claim 1.

19. The method according to claim 18, including at least one of cryopreservation of biological samples and thawing cryopreserved biological samples.

20. The method according to claim 18, further comprising applying a substance to a sample stored in the cavity of the multiwell plate.

21. The method according to claim 20, having at least one of the features
    (a) the substance is a solution which on hardening closes off a surface of the cavity contents from the outside;
    (b) the substance is a natural or synthetic oil, a liquid or a gel which cannot be mixed with an aqueous solution, or is solid carbon dioxide ($CO_2$); and
    (c) the substance has a greater density than a nutrient solution surrounding the sample.

22. The method according to claim 21, wherein the applied substance is a solution which on hardening closes off the surface of the cavity contents from the outside in a gas-tight manner.

23. The method according to claim 20, having at least one of the features
    (a) on thawing of the sample the substance brings about a predetermined reaction or interaction with the sample; and
    (b) the substance is a dilution or washing solution or a cryoprotection agent, acts on the sample as a differentiation factor in relation to the sample, or is a substance which contains antioxidants, anti-apoptosis substances or live/dead staining agents.

24. The method according to claim 21, having at least one of the features
    (a) the substance is applied to the already frozen sample and at least one of after and during thawing of the sample the substance brings about a predetermined reaction or interaction with the sample; and
    (b) the substance is a substance whose condition reveals whether the sample has been frozen or thawed.

* * * * *